(12) United States Patent
Wexell (10) Patent No.: US 6,464,156 B1
(45) Date of Patent: Oct. 15, 2002

(54) MILL, A METHOD FOR PRODUCING BONE TRANSPLANTATION MATERIAL AND USE OF A MILL FOR SUCH PRODUCTION

(75) Inventor: Harry Wexell, Gävle (SE)

(73) Assignee: Lennart Hovelius, Gavle (SE)

( * ) Notice: Subject to any disclaimer, the term of this patent is extended or adjusted under 35 U.S.C. 154(b) by 0 days.

(21) Appl. No.: 08/793,556

(22) PCT Filed: Aug. 21, 1995

(86) PCT No.: PCT/SE95/00947
§ 371 (c)(1),
(2), (4) Date: Feb. 21, 1997

(87) PCT Pub. No.: WO96/05914
PCT Pub. Date: Feb. 29, 1996

(30) Foreign Application Priority Data

Aug. 22, 1994 (SE) .............................................. 9402781

(51) Int. Cl.[7] .............................................. A47J 43/25
(52) U.S. Cl. ...................... 241/93; 241/30; 241/169.1; 241/273.3
(58) Field of Search ...................... 241/30, 93, 169.1, 241/273.3

(56) References Cited

U.S. PATENT DOCUMENTS

| 2,228,025 A | * | 1/1941 | Apflbeck | 146/174 |
|---|---|---|---|---|
| 2,529,473 A | * | 11/1950 | Rustici | 146/82 |
| 2,596,604 A | * | 5/1952 | Schaeffer | 146/82 |
| 2,604,916 A | * | 7/1952 | Mantelet | 146/177 |
| 2,670,019 A | * | 2/1954 | Cuyler | 146/61 |
| 3,907,016 A | * | 9/1975 | Nicholson et al. | 144/172 |
| 4,386,740 A | * | 6/1983 | Van Duersen | 241/93 |
| 5,364,037 A | * | 11/1994 | Bigelow | 241/93 |
| 5,435,237 A | * | 7/1995 | Huang | 99/492 |
| 5,660,341 A | * | 8/1997 | Perkins et al. | 241/93 |
| 5,680,997 A | * | 10/1997 | Hedrington | 241/93 |
| 5,702,061 A | * | 12/1997 | Kennedy et al. | 241/93 |
| 5,879,355 A | * | 3/1999 | Ullmark | 606/93 |

* cited by examiner

Primary Examiner—Allen Ostrager
Assistant Examiner—William Hong
(74) Attorney, Agent, or Firm—Cohn, Powell & Hind, P.C.

(57) ABSTRACT

A mill comprises a casing having an opening for supply of material to be milled and a rotor rotatably supported in the casing and provided with cutting members (3) for disintegrating action on the material. The cutting members (3) are arranged in a plurality of sets (4a–d) distributed about the periphery of the rotor, and having an axial extent (arrow 33). At least two of the sets (4) have their cutting members (3) mutually displaced in axial direction.

22 Claims, 8 Drawing Sheets

MILL, A METHOD FOR PRODUCING BONE TRANSPLANTATION MATERIAL AND USE OF A MILL FOR SUCH PRODUCTION

FIELD OF THE INVENTION AND PRIOR ART

This invention is related to a mill. Furthermore, the invention is related to a method for producing milled bone tissue material intended for transplantation purposes. Finally, the invention is also related to use of a mill for such production.

A very successful method of carrying out transplantations of bone tissue material is based upon filling a cavity in the bone part to be subjected to transplantation entirely or partially with a bone transplant consisting of a bone tissue material, in which the bone tissue occurs as a plurality of small pieces or particles, i.e., in milled or finely divided form. The bone tissue material is imparted a suitable consistency as paste or pulp and suitably contains a liquid, which may comprise tissue liquid, such as blood. In addition, the liquid may contain fat, preferably in the form of living tissue. The transplantation material is packed to a rather solid structure and intergrowth then occurs with the bone tissue of the patient subjected to the transplantation.

Although the transplantation technique in itself has turned out to be successful, it has been connected to great difficulties to produce transplantation material having the adequate structure.

SUMMARY OF THE INVENTION

The object of the present invention is to devise technical solutions, by means of which efficient milling of the material in question may be achieved. In particular, the invention aims at devising constructive measures, by the use of which an optimum structure, for transplantation purposes, of the bone tissue material may be achieved.

This object is obtained by means of the features according to the invention defined in the enclosed claims.

It is in particular pointed out that the mill described herein makes it possible to obtain chips or shavings of perfect structure. During rotation of the rotor, the cutting members will successively cut out these chips or shavings from the bone material under milling at different locations thereof, as a consequence of the mutual displacement of the cutting members in axial direction.

Several advantageous developments are described herein and are discussed more closely in the following.

BRIEF DESCRIPTION OF THE DRAWINGS

With reference to the enclosed drawings, a more close description of an embodiment of the invention cited as an example will follow hereunder.

In the drawings

FIGS. 3 A and B are perspective views of the rotor viewed on its own;

FIG. 9 is a view corresponding to FIG. 7 but illustrating an alternative embodiment.

DETAILED DESCRIPTION OF A PREFERRED EMBODIMENT

Figure 1:
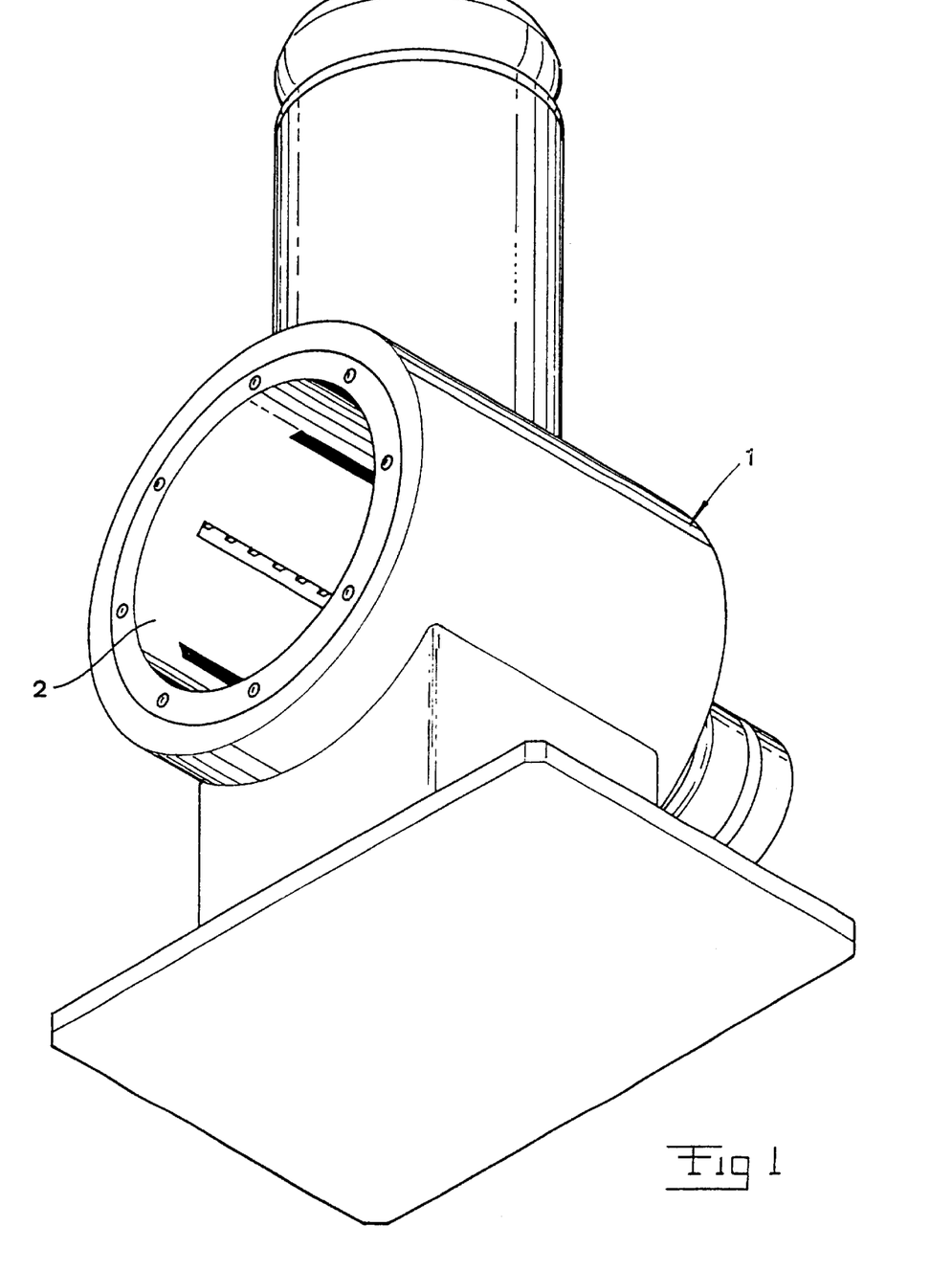
FIG. 1 is a perspective diagrammatical view of the mill according to the invention.
Figure 2:
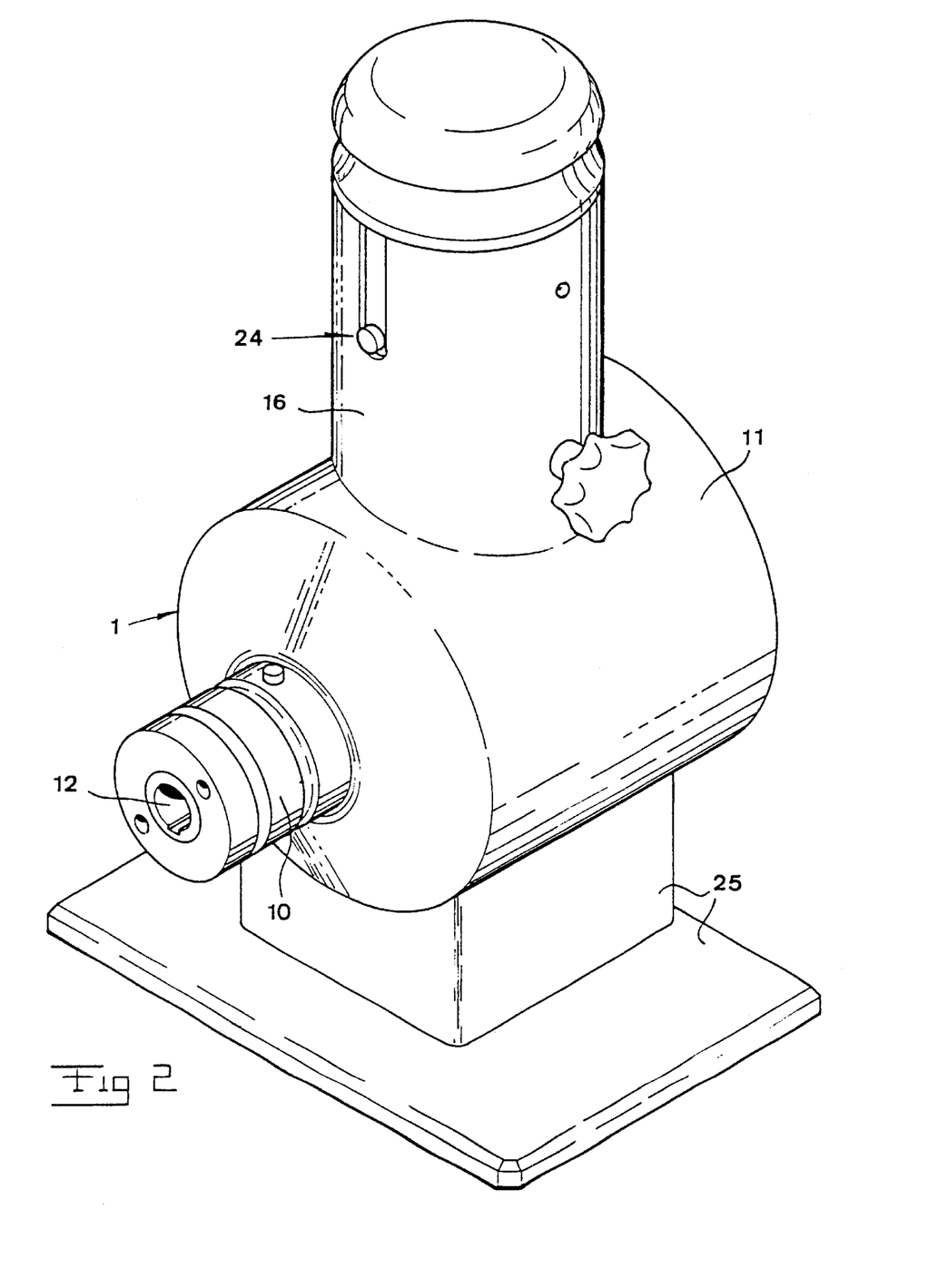
FIG. 2 is a view similar to the view in FIG. 1 but from a diametrically opposite direction.

The mill illustrated in FIGS. 1 and 2 comprises a casing 1 and a rotor 2 rotatably supported therein. The rotor itself is illustrated more closely in FIGS. 3A and 3B. It is provided with cutting members 3 for disintegrating action on the material in question, primarily bone material.

The cutting members 3 are arranged in a plurality of sets 4 distributed about the periphery of the rotor. These sets 4 comprise each one or more cutting members 3. As can be seen, these sets have an axial extent. The term "axial extent" is primarily intended to comprise also such embodiments where the sets may extend obliquely along the periphery of the rotor. However, in the preferred embodiment a complete or at least substantially axial extent of the sets of cutting members is involved.

When several cutting members are present in each individual set 4, the cutting members are mutually separated by interspaces 5. Furthermore, at least two of the sets 4 of cutting member 3 have their cutting members mutually displaced in axial direction. This will be more closely described hereunder with assistance of FIG. 7.

Figure 5:
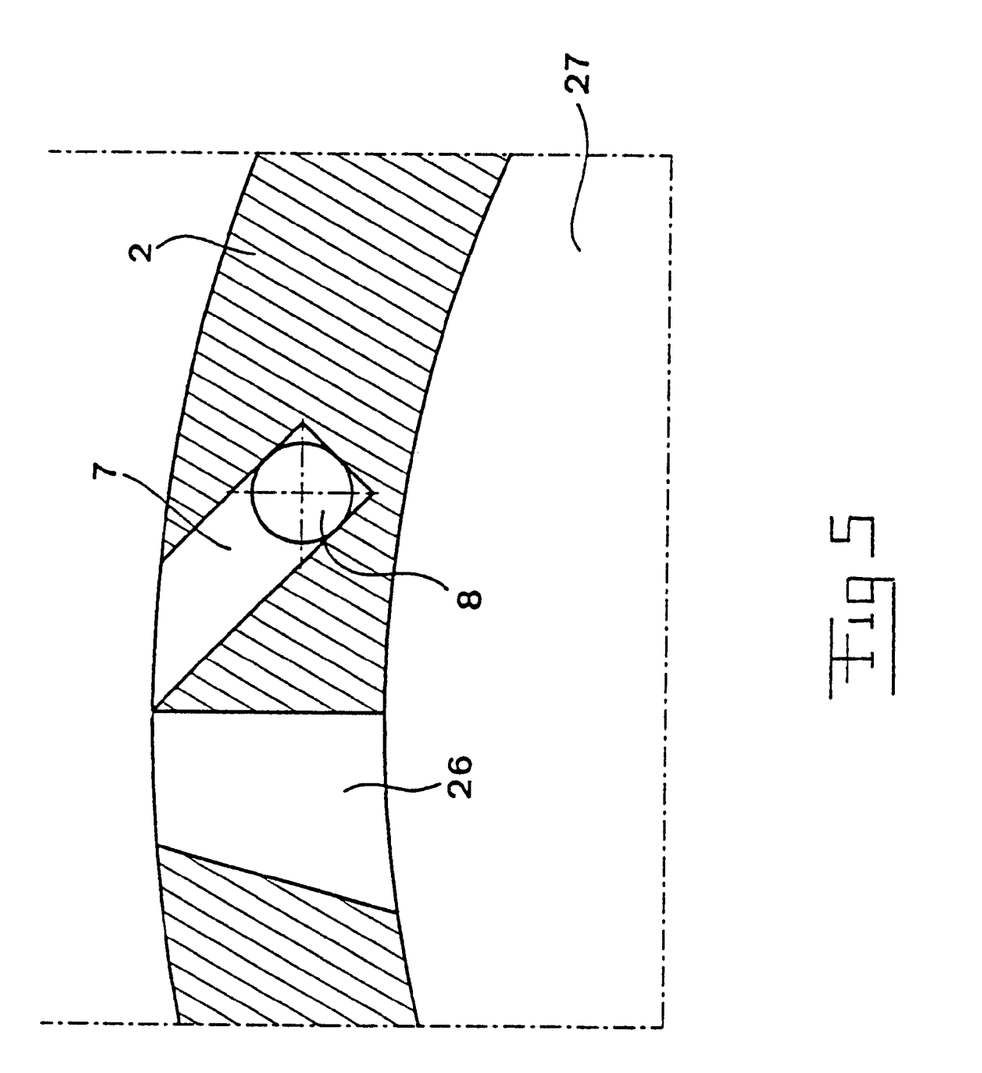
FIG. 5 is an enlarged detail view of a portion of the rotor with cutting members removed.
Figure 6:
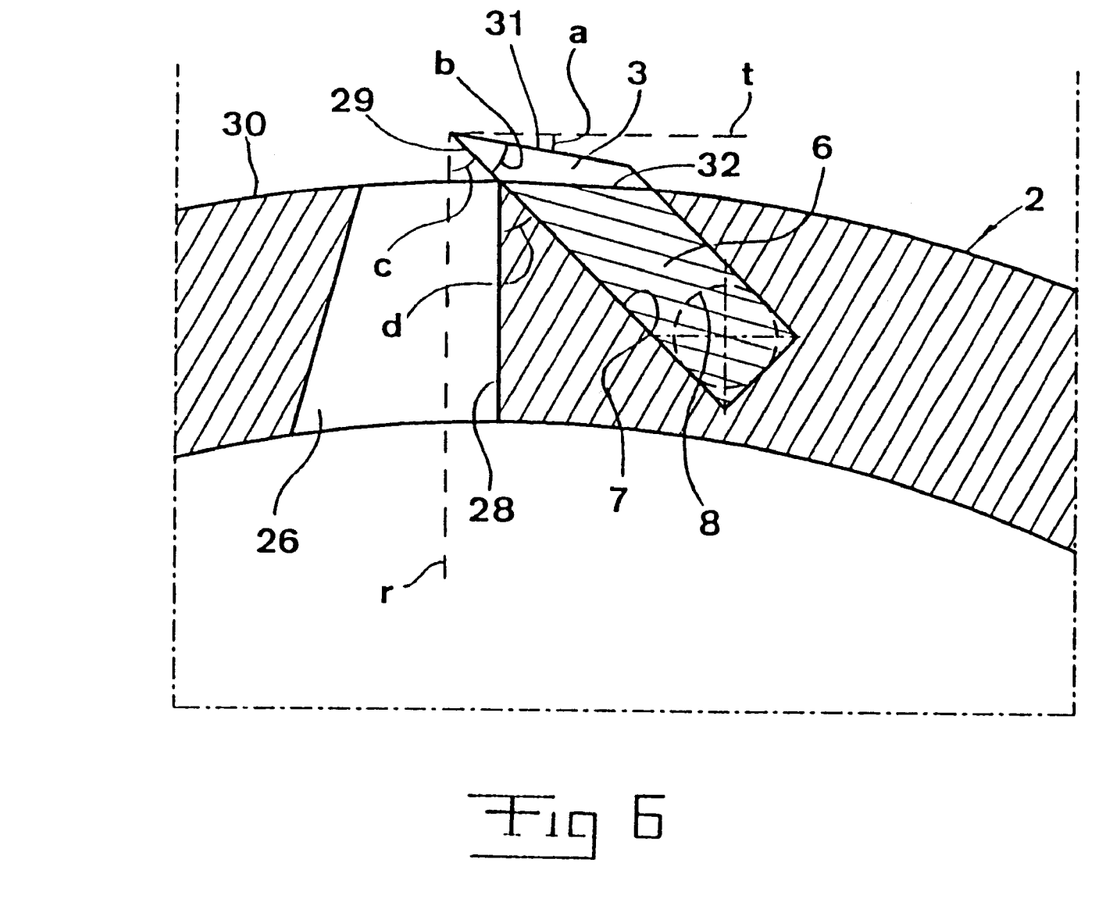
FIG. 6 is a view similar to FIG. 5 but with the cutting members put in place.

The cutting members 3 in an individual set 4 are arranged in a block 6 (see also FIG. 6). This cutting block 6 is removably received in a seat 7 (see also FIG. 5) in the rotor 2. The various cutting members 3 are rigidly secured in the cutting block 6 and the cutting members project with their active cutting portions outwardly of the matrix, suitably of metal, holding the cutting members together. The cutting blocks 6 may be fixed in their associated seats 7 in an arbitrary manner, such as by soldering, gluing, shrinking etc. but the device may also be such that the fitting between the cutting blocks and the seats 7 is such that the cutting blocks are frictionally held in place in the seats.

The rotor 2 comprises one or more openings 8 (see FIGS. 3 and 5–6) for access to the cutting block 6 of tools for actuating the cutting block 6 out of the seat 7. The tool may for instance be constituted by a screw driver or other elongated tool introducable through the openings 8. These openings are arranged in gable sides of the rotor 2 so that, accordingly, each individual cutting block 6 may be actuated at its opposite ends. It is preferred that the openings 8 are normally-closed by means of suitable closure members, for instance screws, so that bone material cannot be collected in the openings.

Figure 3A:
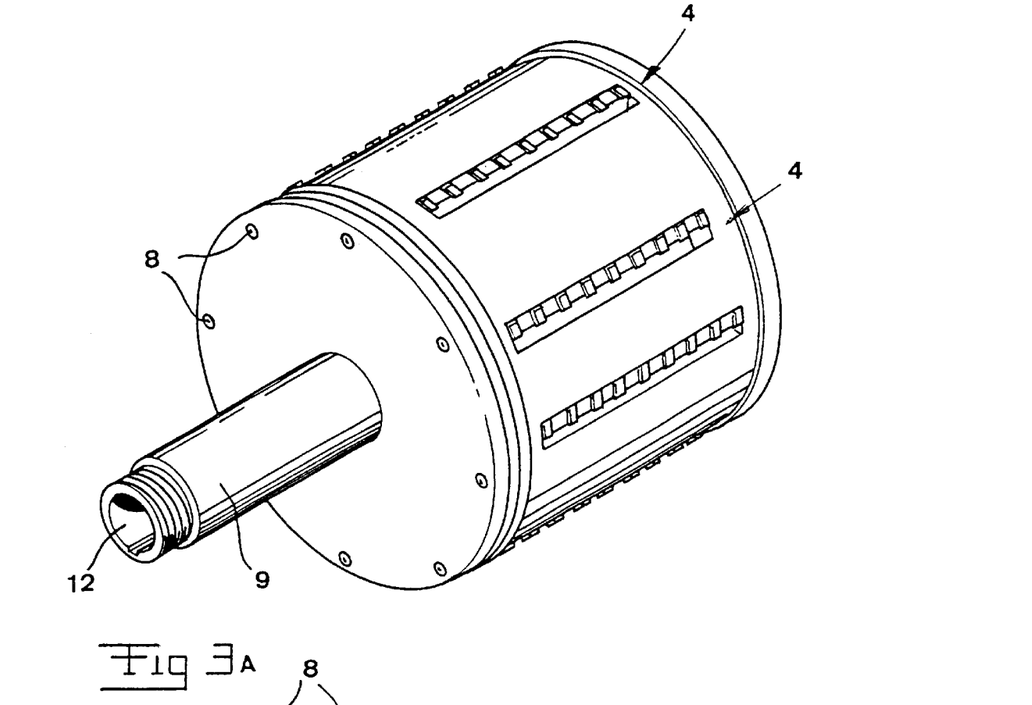
Figure 3B:
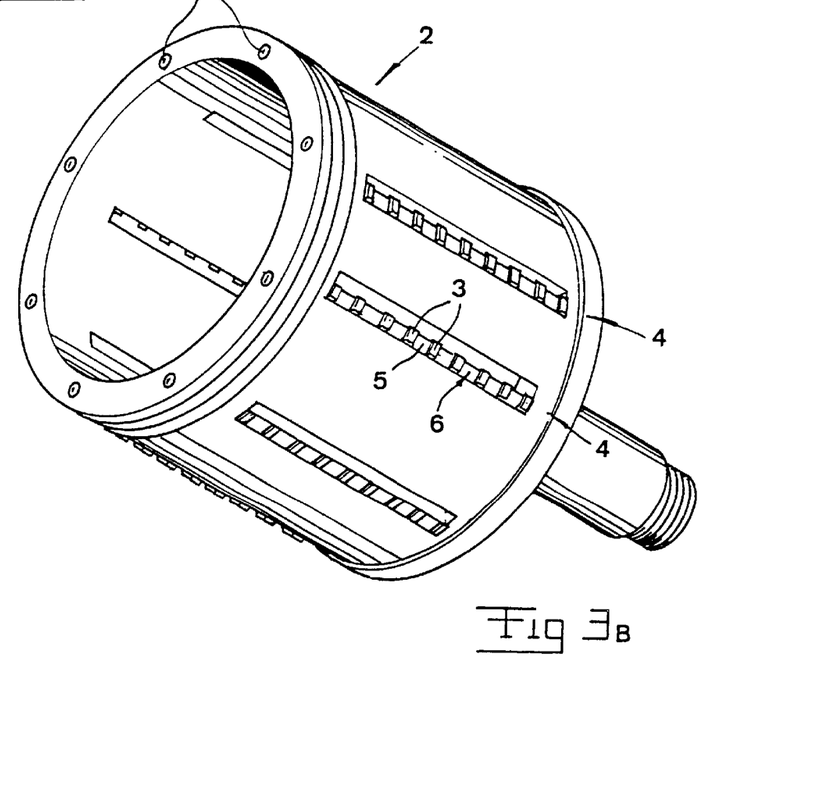

It appears from FIG. 3 that the rotor 2 comprises an axle pin 9 fitting into a bearing sleeve 10 designed on the casing 1. This has a substantially cylindrical main portion 11, in which that part of the rotor 2 which is provided with the cutting members 3 is received.

As seen from FIG. 1, the rotor 2 has one of its ends, more specifically that end which is opposite to the axle pin 9, open and the main portion 11 of the casing is likewise open at that place so that the milled material can exit the rotor and the casing at this end and subsequently arrive in some suitable receptacle placed thereunder.

Such an open design is, however, not necessary but the casing could be closed also at the end which is now open with exception of a smaller outlet opening. The end 12 of the axle pin 9 is intended to be coupled to some suitable driving element. In a more simple embodiment, this element may be formed by a crank intended to be driven by hand power and in more complex embodiments, the end 12 may be coupled to a suitable drive motor.

Figure 4:
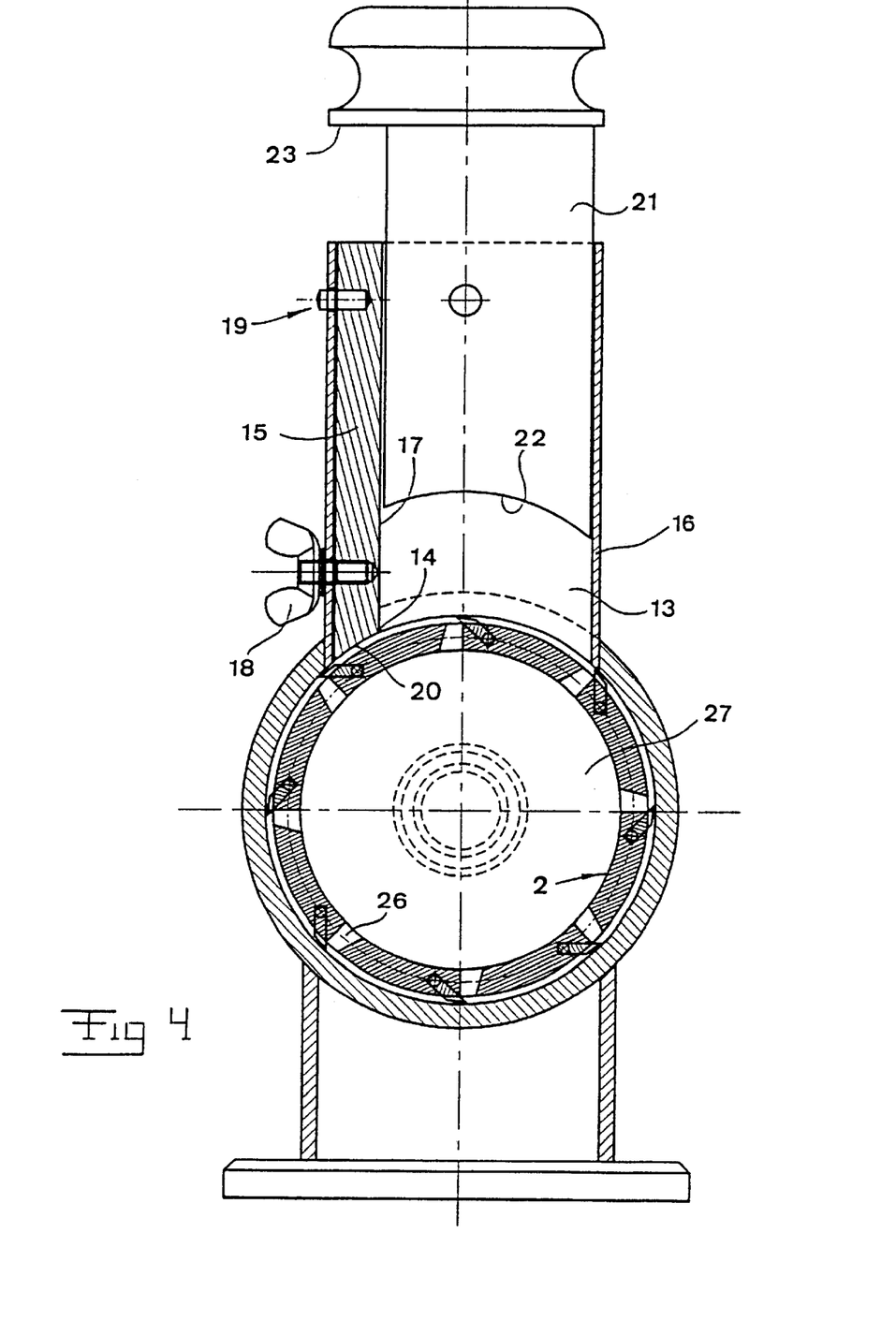
FIG. 4 is a section through the mill taken perpendicularly to the axis of rotation of the rotor.

It appears from FIG. 4 that the material to be milled may be supplied to the rotor 2 via a supply opening 13. This opening is delimited, most closely to the periphery of the rotor 2, by an edge 14, which meets the cutting members 3 and which has a substantially straight and axial extent. This edge 14 is formed on an insert 15, which is secured in a tubular portion 16 of the casing, said tubular portion participating in formation of the supply opening 13.

The insert 15 has a substantially planar surface 17 turned towards the supply opening 13. For the rest the insert 15 has a surface which is curved in correspondence to the curved inner surface of the tubular portion 16, which is cross-sectionally circular. The insert 15 is secured in place by means of a suitable securing member 18, for instance a locking screw. Further locating means 19 may be present, for instance in the form of a pin 19 formed on the insert 15 and received in a hole formed in the tubular portion 16.

Thus, the edge 14 will operate as a counter holding element to the material which is to be milled as the cutting members move past the edge.

The insert 15 has a surface 20 turned towards the rotor 2, said surface being curved in correspondence to the periphery of the rotor and being located just outside the circle described by the edges of the cutting members.

A press member 21 is movably received in the supply opening 13 with a portion having a cross-section designed in correspondence to the cross-section of the supply opening 13 and a surface 22 turned towards the rotor 2 curved in correspondence to the periphery of the rotor. There are means for restricting the movement downwardly of the press member in the opening 13. This means may for instance be formed by an abutment surface 23 on the press member, said surface being intended to obtain support against the upper end of the tubular portion 16. The press member 21 is prevented from rotating in the opening 13 as a consequence of their unround cross-section. Further means may be present for such restriction of rotation, namely those which are denoted 24 in FIG. 2 and which here consists of a slot formed in the tubular portion 16 and a pin received in this slot and designed on the press member 21.

For the rest the casing 11 is provided with a support device 25 suitable for supporting the mill relative to a suitable under layer.

The rotor 2 comprises (FIGS. 4–6) slots 26 for material passage to an internal space 27 in the rotor, said slots being present ahead of the cutting members 3 in the various sets as viewed in the direction of the rotation. The cutting members 3 are arranged in immediate connection to those slots 26 so that an axial delimiting side 28 of these slots will adjoin substantially directly to the breast surface 29 of the cutting members 3 at the peripheral mantle surface 30 of the rotor 2 (FIG. 6).

It is preferred that the slots 26 widen from the mantle surface 30 of the rotor 2 in the direction towards the inner space 27 of the rotor. The delimiting side 28 already mentioned may be oriented substantially radially whereas widening of the slot is provided by the opposite delimiting side of the slot.

The angle a of clearance of the individual cutting member defined as the angle between the back surface 31 of the cutting member and the tangent t is in the interval 1–20°, preferably 2–16°, and in particular 4–10°. The angle a of clearance is about 6° in the example.

The tool angle b of the cutting member defined as the angle between the breast surface 29 of the cutting member and the back surface 31 is 20–60°, preferably 30–50°, and in particular 35–40°. The tool angle is about 39° in the example.

The chipping angle c of the cutting member 3 defined as the angle between the breast surface 29 of the cutting member and a radius r of the rotor is 20–70°, suitably 30–60° preferably 40–50°, and in particular about 45°.

The angle d between the breast surface 29 of the cutting member 3 and the adjacent delimiting side 28 of the chip slot 26 is 25–65°, preferably 35–55°, and in particular 40–50°. The angle d is about 45° in the example.

The cutting blocks 6 are designed such that their matrix has an external surface 32 between adjacent projecting parts of two cutting members 3, said external surface 32 substantially corresponding to the mantle surface 30 of the rotor 2 by means of a curvature provided in correspondence thereto or planarity obtained tangentially thereto.

The effective cutting width B (FIG. 7) of the cutting members 3 such that they diagrammatically appear from said figure is preferably within the interval 0.5–4 mm. A width within the interval 1–3 mm is preferred. In the embodiment discussed, the cutting width B is substantially 2 mm. The interspace 5 between two adjacent cutting members 3 varies depending upon the number of sets 4 of cutting members. According to the invention, the number of sets of cutting members, the number of cutting members 3 in each set, the cutting width B of each cutting member and the mutual displacement of the cutting members of the various sets in axial direction are adjusted in order to achieve that the cutting members 3 shall be capable of cutting at least one continuos material layer from the material which is milled on one revolution of the rotor 2.

Figure 7:
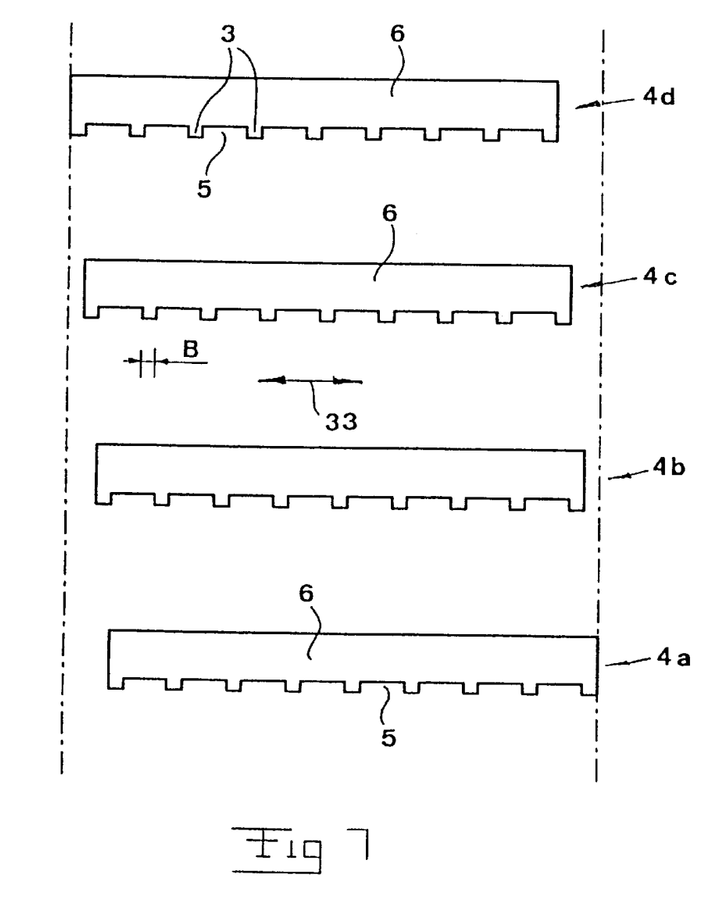
FIG. 7 is a diagrammatical view where the mantle surface of the rotor is conceived to be spread out to a plane state and illustrated with chain-dotted lines, the axial position for four different cutting blocks being illustrated.

The rotor comprises, in the example, eight cutting blocks 6 in total, four being illustrated in FIG. 7. These four cutting blocks 6 are conceived to have an effective cutting width B of the cutting members of 2 mm and interspaces 5 of 6 mm. The various cutting blocks 6 are here of an identical design. In order to obtain the axial mutual displacement of the cutting members 3 of different sets 4, the various cutting blocks 6 are displaced in axial direction (arrow 33) so that the axial displacement between two adjacent cutting blocks 6 is 2 mm. The displacement occurs successively as illustrated in FIG. 7. The essence of this is that an interspace 5 between two cutting members of a set 4a which is the foremost as viewed in the direction of rotation of the cutting member sets will leave a ridge in the material under milling, said ridge being run over in succession by the cutting members of the sets 4b, 4c and 4d arriving thereafter. Thus, these four sets of cutting members will peel off a complete bone layer from the bone material under milling.

Since as mentioned there are eight sets of cutting members on the rotor in the example, the rotor will peel off, during one revolution of the rotor, two layers of bone material from the material under milling.

Figure 8:
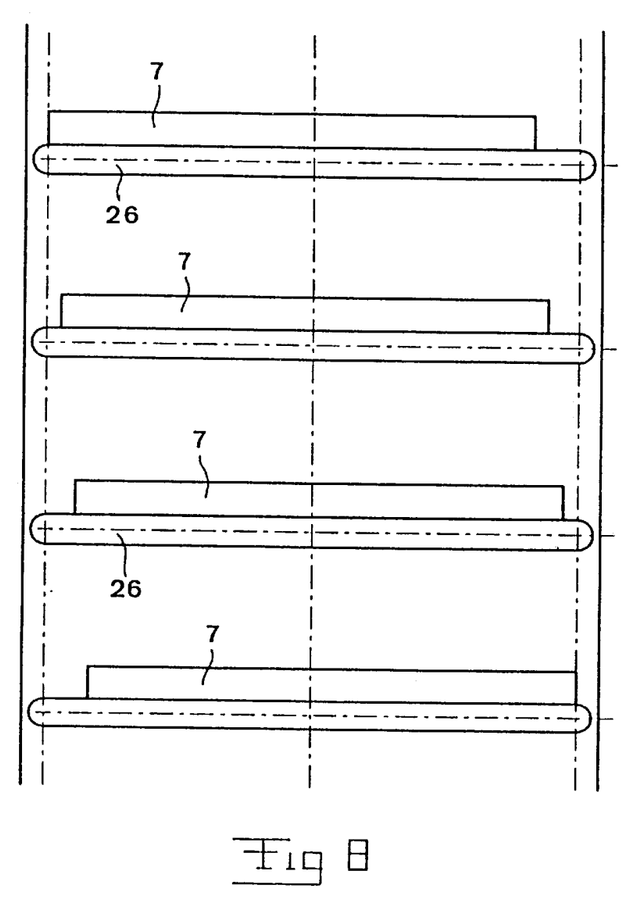
FIG. 8 is a view, which illustrates, also diagrammatically, the mantle of the rotor spread out in a plane but, in addition, the seats for the various cutting blocks illustrated in FIG. 7 are illustrated in FIG. 8 and also the chip slots arranged in the rotor for these cutting blocks.

Since the cutting blocks 6 are entirely identical as mentioned it is required that the various seats 7 (FIG. 8) for them are located displaced on the rotor to a corresponding degree. The chip slots 26 may, if so desired, have an equal design for all seats 7.

An alternative embodiment is illustrated in FIG. 9. Knife blocks are there instead of different design. As can be seen, the knife blocks 6a–d have their cutting members 3 placed differently on the blocks. The axial mutual displacement of the cutting members 3 is here instead obtained by all cutting blocks having the same axial position on the rotor. In this embodiment the effective cutting width of the cutting members and the interspaces between the cutting members are chosen in correspondence to what has been described with assistance of FIG. 7.

In use of the mill according to the invention, the rotor is caused to rotate and bone material to be milled is introduced into the supply opening 13 and actuated by the press member 21 towards the rotor. As the rotor sweeps past the supply opening 13, the cutting members 3 will cut out chips from the bone material layer by layer as milling continues. The features defined of the mill ensure that the chip material obtained will be extremely well suited to function for transplantation purposes.

The mortise chisel like design of the cutting members 3 yields a lenient processing of the bone and a good quality of the bone substance.

The counter sinking of the cutting members 3 in the rotor is formed so exactly that further securing is not necessary and no bone residuals may remain, which among others enables efficient cleaning of the rotor.

The counter element 14; 15 enables milling where a smaller amount of force is required and makes sure, together with outer details in the construction of the rotor, that motor power is not necessarily required.

The invention is of course not only restricted to the embodiment described. Thus, numerous modifications may be made within the scope of invention.

What is claimed is:

1. A mill comprising a casing (1) having an opening (13) for supply of material to be milled and a rotor (2), which is rotatably supported in the casing and provided with cutting members (3) for disintegrating action on the material, characterized in that the cutting members (3) are arranged in a plurality of sets (4) having an axial extent and being distributed about the periphery of the rotor, that the cutting members (3) in each individual set are mutually displaced with interspaces (5) and that the sets (4) of cutting members (3) having their cutting members mutually displaced in axial direction so that the same effective cutting is achieved all over the material width, the cutting members (3) in an individual set (4) being arranged in a block (6), and the block (6) being removably received in a seat (7) of the rotor (2).

2. A mill according to claim 1, characterized in that the mutual displacement in axial direction of the cutting members (3) in said sets (4) is substantially equally as large as the effective cutting width (B) of the cutting members.

3. A mill according to claim 1, characterized in that the cutting members (3) have a substantially equal effective cutting width (B).

4. A mill according to claim 1, characterized in that the number of sets (4) of cutting members (3), their cutting width (B) and the mutual displacement of the cutting members in axial direction are adjusted to achieve that the cutting members should be capable of cutting, on one revolution of the rotor, at least one material layer from the material which is being milled.

5. A mill according to claim 1, characterized in that the cutting blocks (6) have an equal design but are arranged mutually displaced in the rotor, at least as far as some of them are concerned, in axial direction.

6. A mill according to claim 1, characterized in that the cutting blocks (6) are arranged in an equal manner on the rotor as far as axial position is concerned but that at least some of the blocks have their cutting members differently located as far as axial position is concerned.

7. A mill according to claim 1, characterized in that the rotor (2) comprises one or more openings (8) for access to the cutting block of tools for actuation of the cutting block (6) out of the seat (7).

8. A mill according to claim 1, characterized in that the tool angle (b) of the cutting member is 20–60°.

9. A mill according to claim 8 characterized in that the tool angle (b) of the cutting member is 30–50°.

10. A mill according to claim 8 characterized in that the tool angle (b) of the cutting member is 35–45°.

11. A mill according to claim 1, characterized in that the chipping angle (c) of the cutting member is 20–70°.

12. A mill according to claim 11 characterized in that the chipping angle (c) of the cutting member is 30–60°.

13. A mill according to claim 11 characterized in that the chipping angle (c) of the cutting member is 40–50°.

14. A mill according to claim 1, characterized in that the angle (a) of clearance of the cutting member is 1–20°.

15. A mill according to claim 4 characterized in that the angle (a) of clearance of the cutting member is 2–16°.

16. A mill according to claim 4 characterized in that the angle (a) of clearance of the cutting member is 4–10°.

17. A mill according to claim 1, characterized in that the supply opening (13) is delimited by an edge (14) meeting the cutting members (3), said edge having a substantially straight and axial extent.

18. A mill according to claim 17, characterized in that the edge (14) is shaped on an insert (15), which is secured in a tubular portion (16) of the casing, said tubular portion participating in formulation of the supply opening.

19. A mill according to claim 18, characterized in that the insert (15) has a substantially planar surface (17) turned towards the supply opening.

20. A mill according to claim 1, characterized in that the rotor comprises, ahead of the cutting members in the various sets as viewed in the direction of rotation, slots (26) for passage of material to an inner space (27) of the rotor.

21. A mill comprising a casing (1) having an opening (13) for supply of material to be milled and a rotor (2), which is rotatably supported in the casing and provided with cutting members (3) for disintegrating action on the material, characterized in that the cutting members (3) are arranged in a plurality of sets (4) having an axial extent and being distributed about the periphery of the rotor, that the cutting members (3) in each individual set are mutually displaced with interspaces (5) and that the sets (4) of cutting members (3) having their cutting members mutually displaced in axial direction so that the same effective cutting is achieved all over the material width, the cutting members (3) in an individual set (4) being arranged a block (6), and the block (6) being removably received in a seat (7) of the rotor (2) and the rotor (2) comprising one or more openings (8) for access to the cutting block of tools for actuation of the cutting block (6) out of the seat (7) and the openings (8) being arranged in gable sides of the rotor.

22. A method for production of milled bone tissue material intended for transplantation purposes, a mill being used, which has a casing provided with an opening (13) for supply of bone material to be milled and a rotor (2) rotatably supported in the casing and provided with cutting members (3) for disintegrating action on the bone material, characterized in that the method includes the steps of arranging the cutting members (3) in a plurality of sets (4) having an axial extent and distributing the sets about the periphery of the rotor, mutually displacing the cutting members (3) in each individual set with interspaces (5) and that the sets (4) of cutting members (3) have their cutting members mutually displaced in axial direction so that the same effective cutting is achieved all over the material width.

\* \* \* \* \*